(12) United States Patent
Baumann

(10) Patent No.: US 8,663,147 B2
(45) Date of Patent: Mar. 4, 2014

(54) TREATMENT OF THROMBOANGIITIS OBLITERANS BY REMOVAL OF AUTOANTIBODIES

(76) Inventor: Gert Baumann, Berlin (DE)

( * ) Notice: Subject to any disclaimer, the term of this patent is extended or adjusted under 35 U.S.C. 154(b) by 0 days.

(21) Appl. No.: 12/988,267

(22) PCT Filed: Apr. 20, 2009

(86) PCT No.: PCT/EP2009/002993
§ 371 (c)(1),
(2), (4) Date: Dec. 15, 2010

(87) PCT Pub. No.: WO2009/143944
PCT Pub. Date: Dec. 3, 2009

(65) Prior Publication Data
US 2011/0105980 A1 May 5, 2011

(30) Foreign Application Priority Data
Apr. 18, 2008 (EP) .................... 08075309

(51) Int. Cl.
*A61M 37/00* (2006.01)
(52) U.S. Cl.
USPC ........................................ 604/5.01
(58) Field of Classification Search
USPC ........................................ 604/5.01
See application file for complete search history.

(56) References Cited

U.S. PATENT DOCUMENTS

| 6,551,266 | B1   | 4/2003  | Davis          |         |
|-----------|------|---------|----------------|---------|
| 7,022,322 | B2 * | 4/2006  | Koll et al.    | 424/140.1 |
| 2003/0175274 | A1 * | 9/2003  | Rosen et al.   | 424/145.1 |
| 2008/0040153 | A1   | 2/2008  | Davis          |         |
| 2009/0246203 | A1   | 10/2009 | Lueking et al. |         |
| 2010/0047211 | A1 * | 2/2010  | Mcniece        | 424/93.7 |
| 2010/0129318 | A1 * | 5/2010  | O'Neil et al.  | 424/85.2 |

FOREIGN PATENT DOCUMENTS

| DE | 102006003782 A1 | 8/2007 |
| WO | 9717980 A1 | 5/1997 |
| WO | 0038760 A2 | 7/2000 |
| WO | 2007/085240 A1 | 8/2007 |
| WO | 2008151847 A1 | 12/2008 |
| WO | WO 2008151847 A1 * | 12/2008 |

OTHER PUBLICATIONS

Richter et al., "Efficacy and safety of immunoglobulin apheresis" in Medline, Jan. 1, 1997.
Database WPI Week 20012; Thomson Scientific, London, GB; An 2001-014113, XP002575838, & RU 2 153 168 C2 (Cardiology Res Inst), Jul. 20, 2000, Abstract.
Database WPI Week 19893, Thomson Scientific, London, GB; An 1989-022467, XP002576173, & SU 1 409 245 A1 (Tomsk Med Inst), Jul. 15, 1988, Abstract.

(Continued)

*Primary Examiner* — Susan Su
*Assistant Examiner* — Guy K Townsend
(74) *Attorney, Agent, or Firm* — Joyce von Natzmer; Agris & von Natzmer LLP

(57) ABSTRACT

The invention relates to the use of a specific ligand for antibodies, preferably autoantibodies in the manufacture of a column for the treatment of thromboangiitis obliterans. The invention pertains furthermore to the apheresis column with at least one anti-IgG antibody for the treatment of thromboangiitis obliterans.

14 Claims, 11 Drawing Sheets

(56) References Cited

OTHER PUBLICATIONS

Database Medline [Online], US National Library of Medicine (NLM), Bethesda, MD, US; Jun. 2007, Ponticelli C: "De novo thrombotic microangiopathy. An underrated complication of renal transplantation," XP002575839, Database accession No. NLM17598367, Abstract.

Database Biosis [Online], Biosciences Information Service, Philadelphia, PA, US; Nov. 1999, YEH J-H et al: "Double filtration plasmapheresis in myasthenia gravis: Analysis of clinical efficacy and prognostic parameters," XP002575840; Database accession No. PREV200000005576, Abstract.

Database Biosis [Online], Biosciences Information Service, Philadelphia, PA, US; Apr. 4, 2006, Koll Robert et al.: "Treatment of cardiomyopathy by removal of autoantiboides," XP002575841, Database accession No. PREV200600362790. Abstract.

Database Medline [Online], Medical Department II, University of Munich, Germany; Jan.-Feb. 1997, Richter et al.: "Efficacy and safety of immunoglobulin apheresis," XP002492543, Database accession No. NLM9116354, Abstract.

Papa M. et al.: "Autoimmune mechanisms in thromboangiitis obliterans (Buerger's disease): The role of tobacco antigen and the major histocompatibility complex" in: Surgery, vol. 111, No. 5, 1992, pp. 527-531.

Zhang, Y. et al.: "Treating Principles and Methods of Traditional Chinese Medicine in Treatment of Peripheral Vascular Diseases" in: Journal of Traditional Chinese Medicine, 2001, vol. 21, No. 2, 312-313.

Papa M. et al.: "Autoimmune mechanisms in thromboangiitis obliterans Buerger's disease: The role of tobacco antigen and the major histocompatibility complex" Abstract PREV199294028735.

Puëchal and Fiessinger: "Thromboangiitis obliterans or Buerger's disease: challenges for the rheumatologist,"Rheumatology 2007;46:192-199 (Nov. 20, 2007).

* cited by examiner

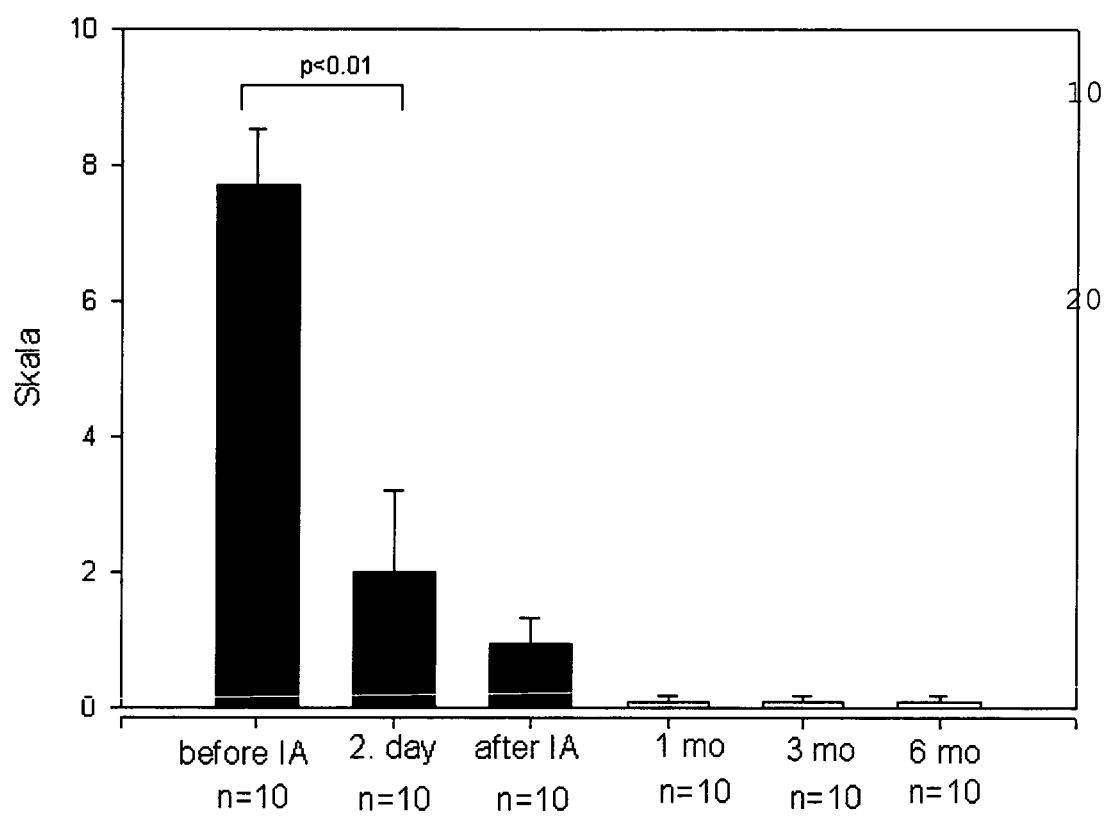
Figure 1: pain scale (1-10)

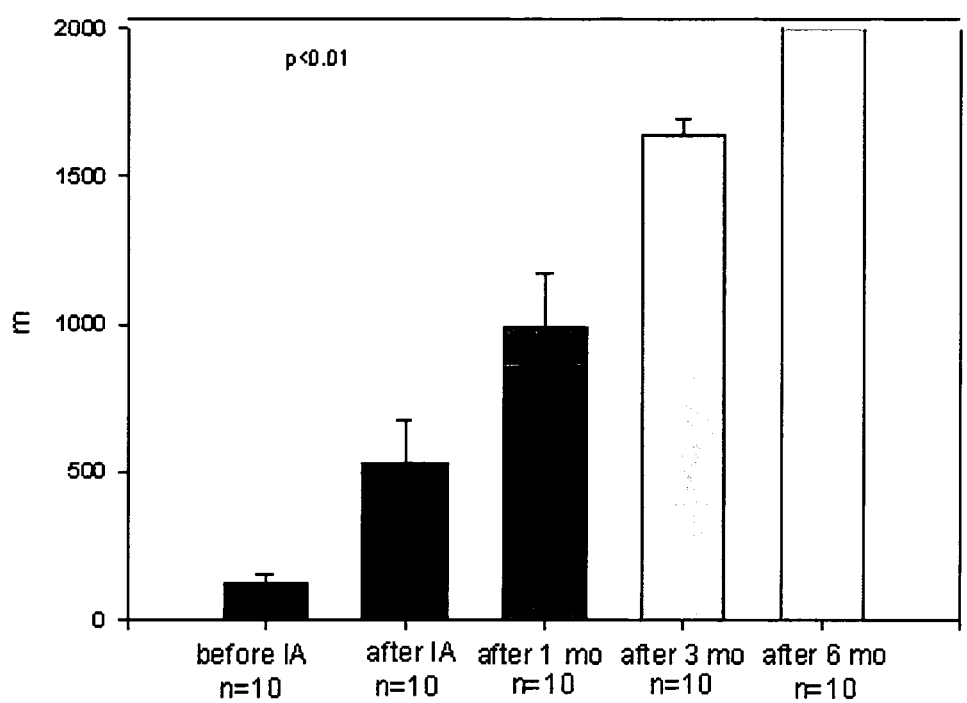

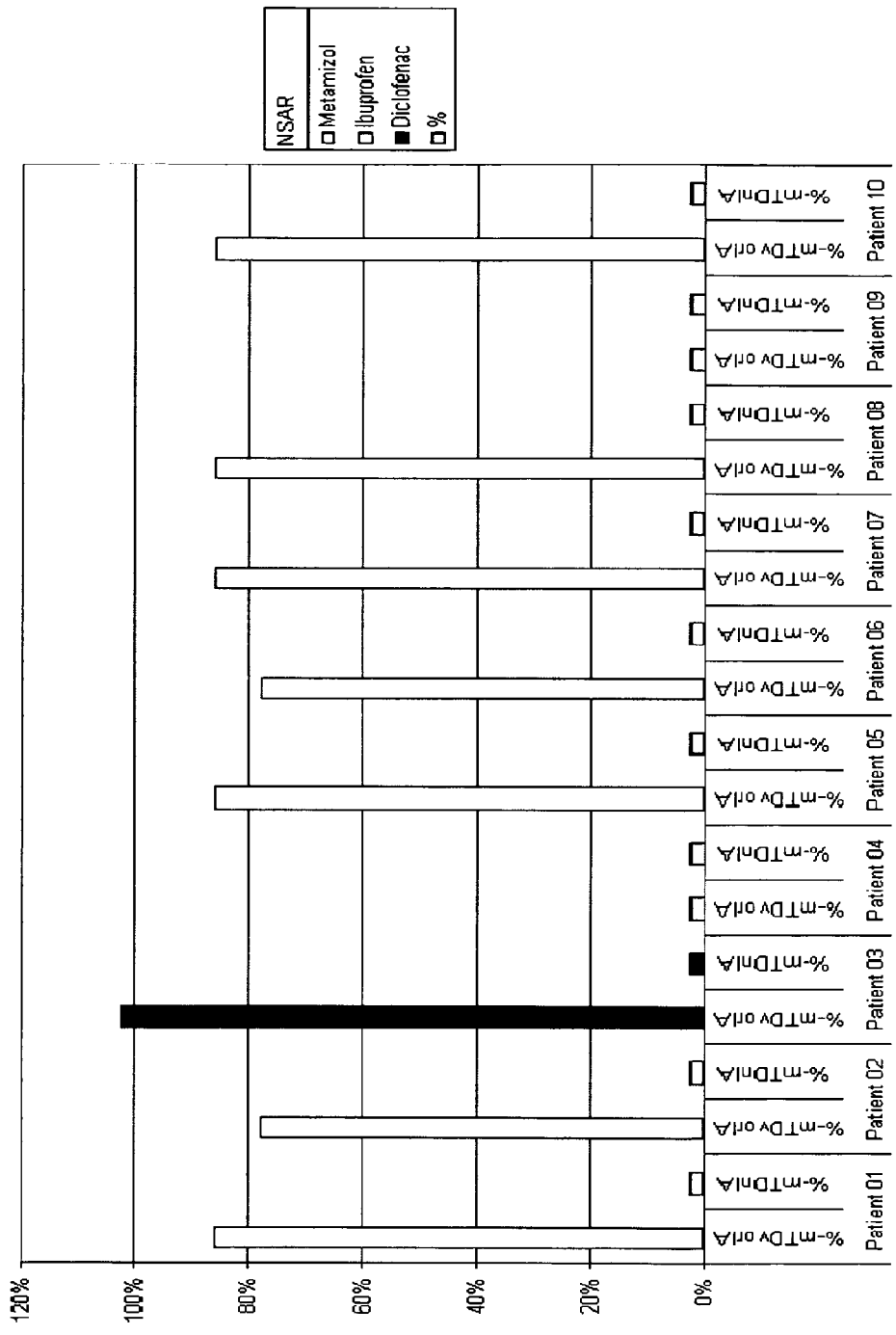
Figure 3: Use of pain reliever NSAR prior and post IA

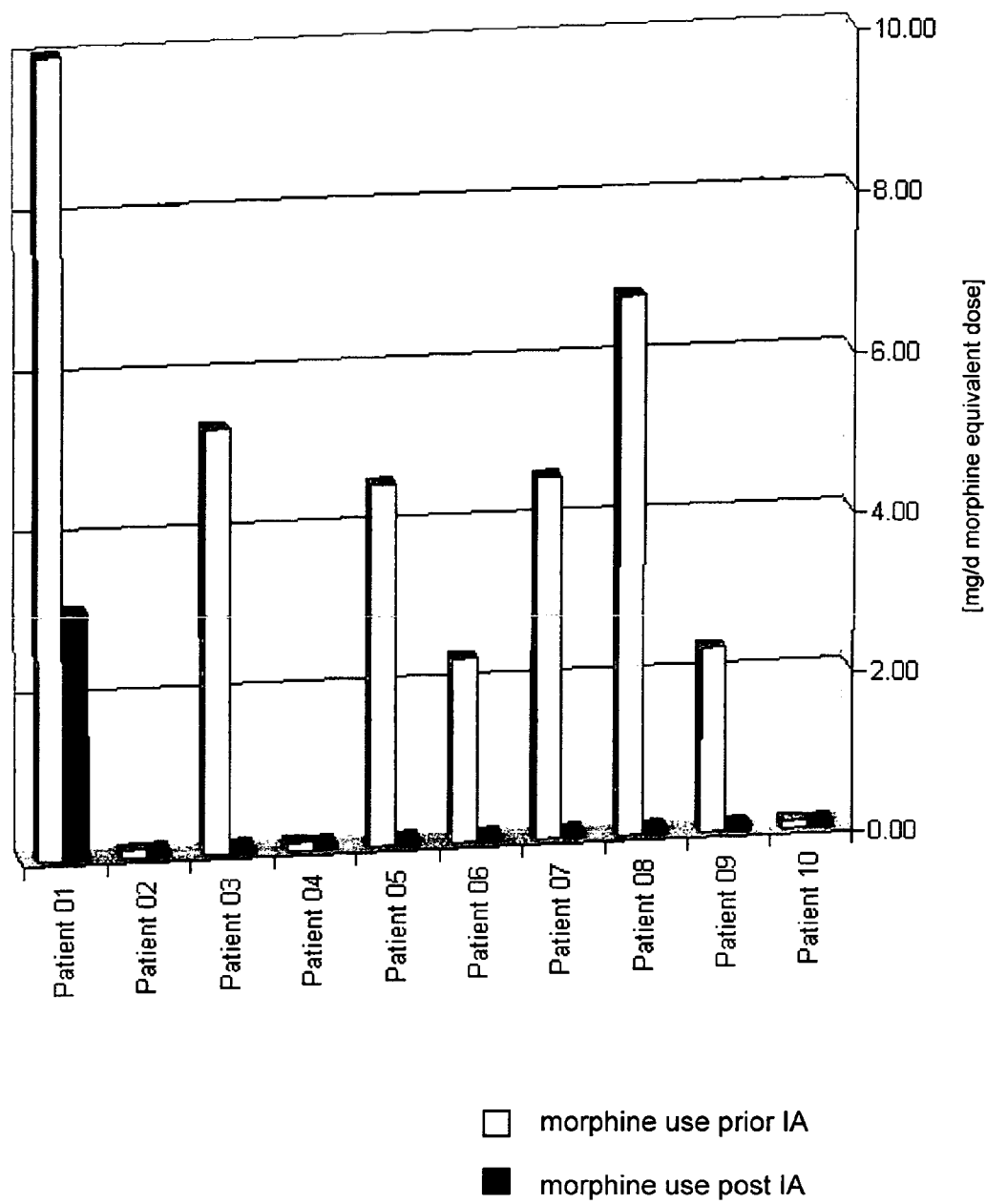
Figure 4: Use of pain reliever opioids prior and post IA

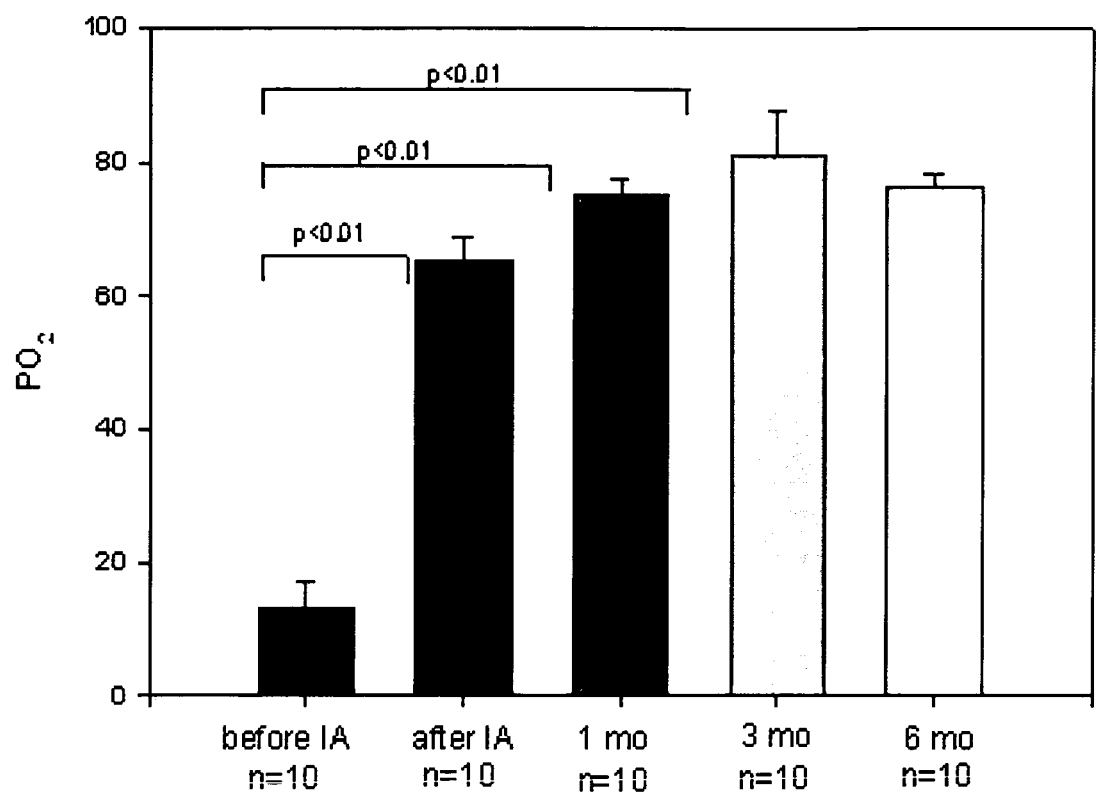
Figure 5: PO2 right foot

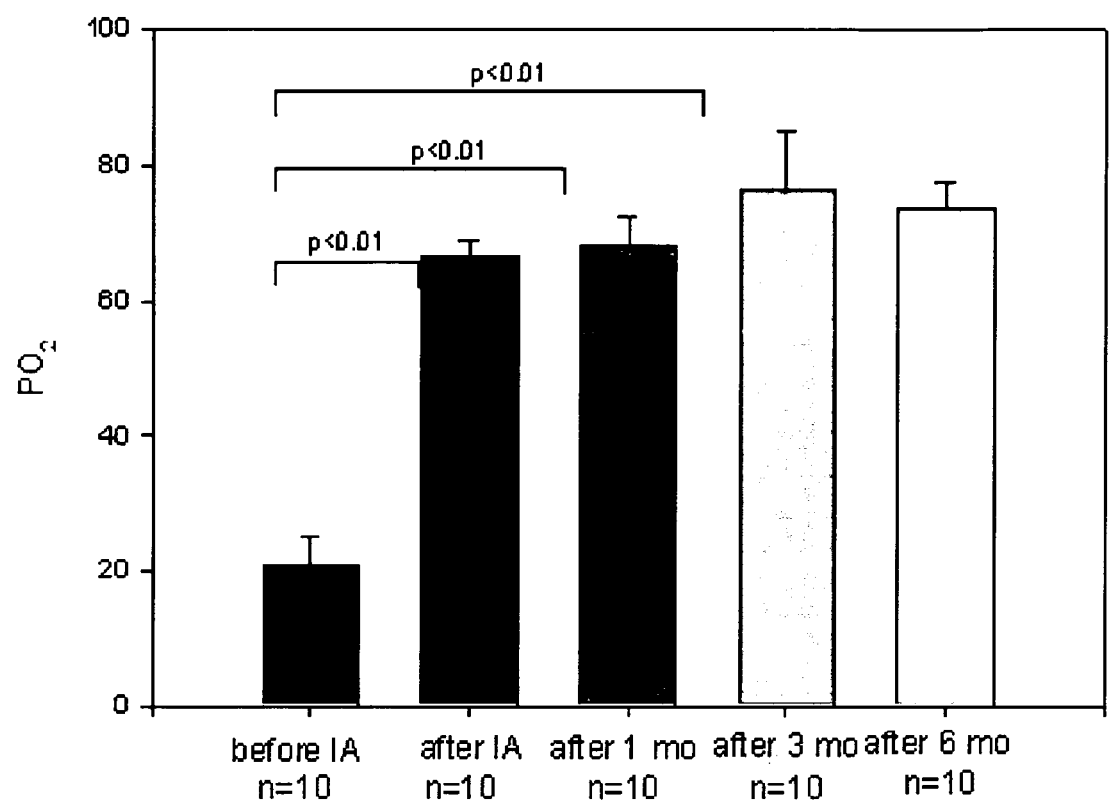
Figure 6: PO2 left foot

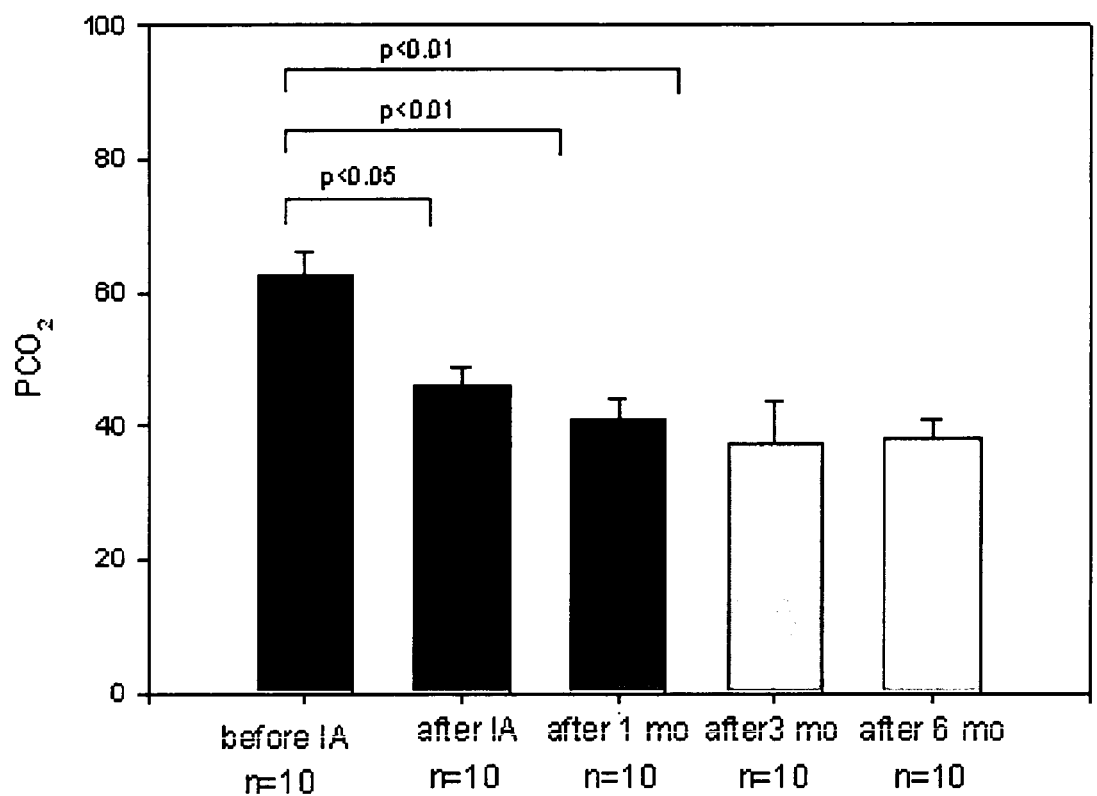
Figure 7: PCO2 right foot

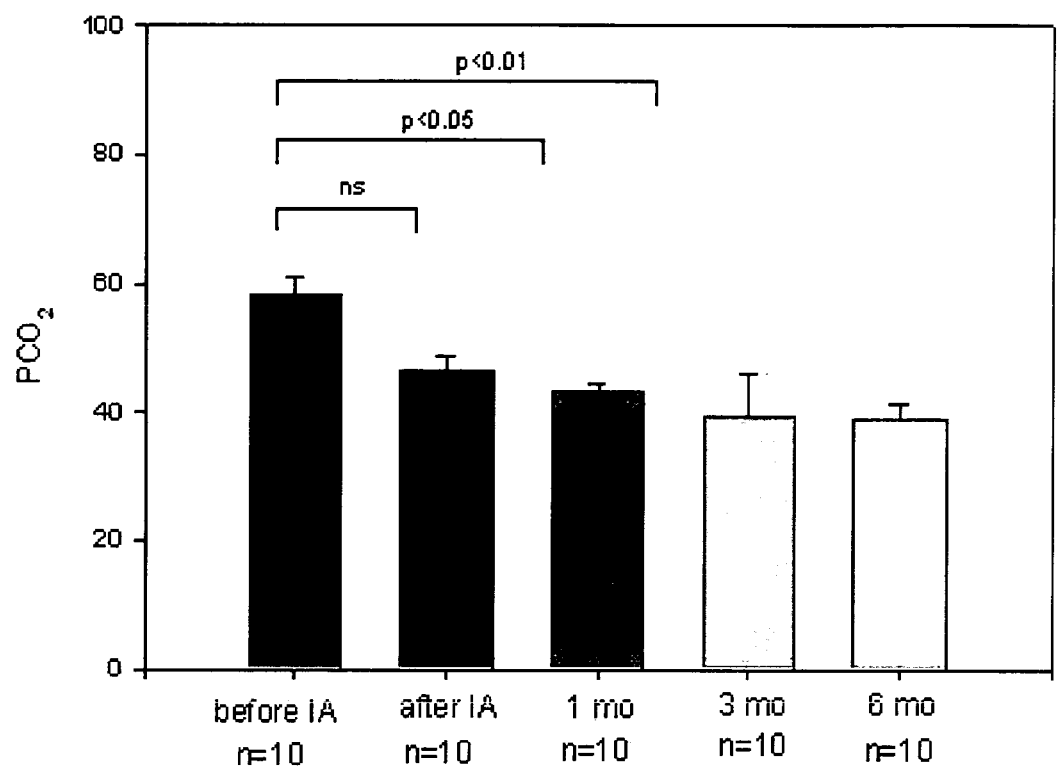
Figure 8: PCO2 left foot

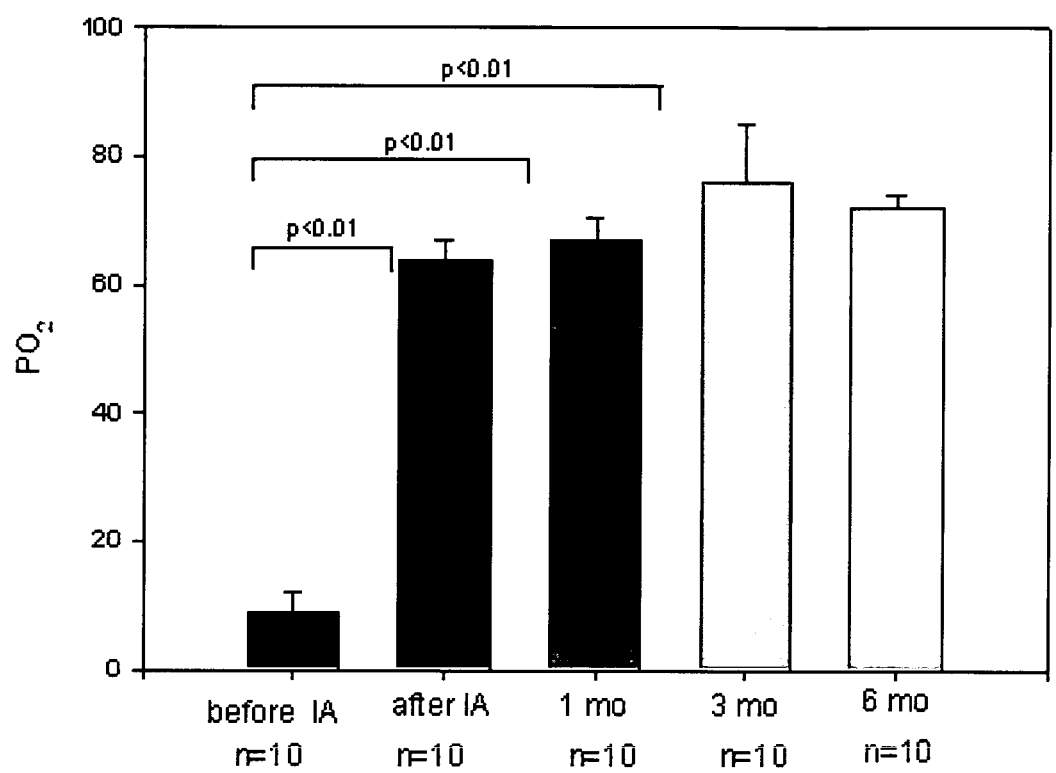
Figure 9: PO2 most affected extremity

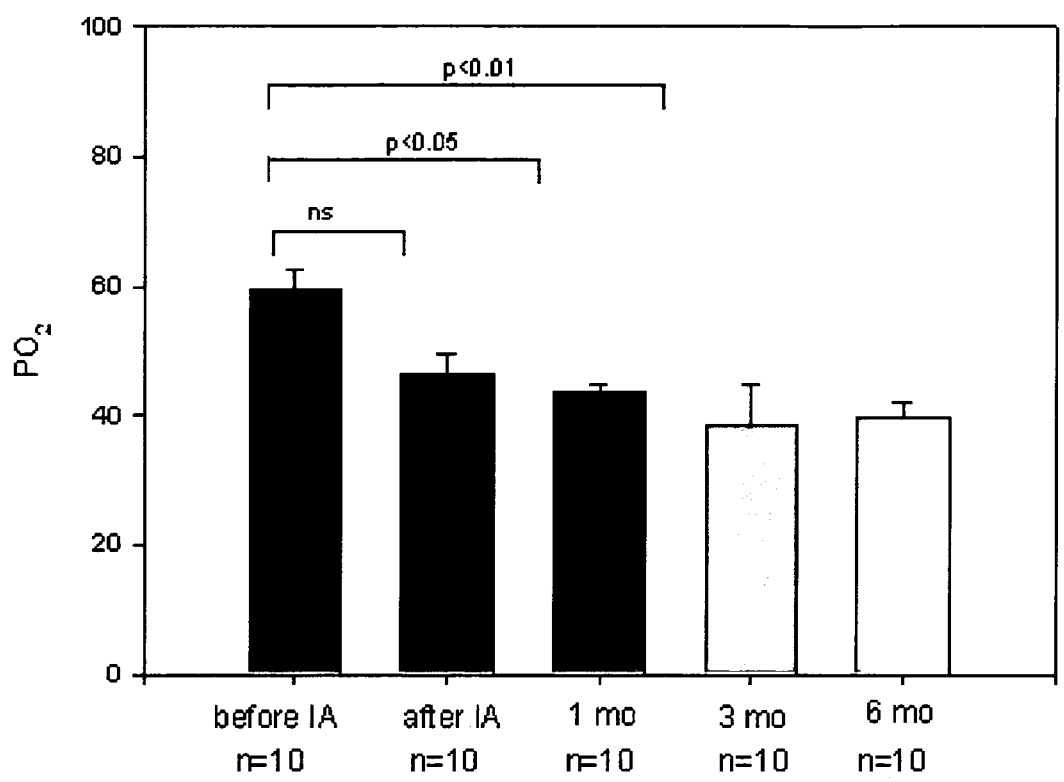
Figure 10: PCO2 most affected extremity

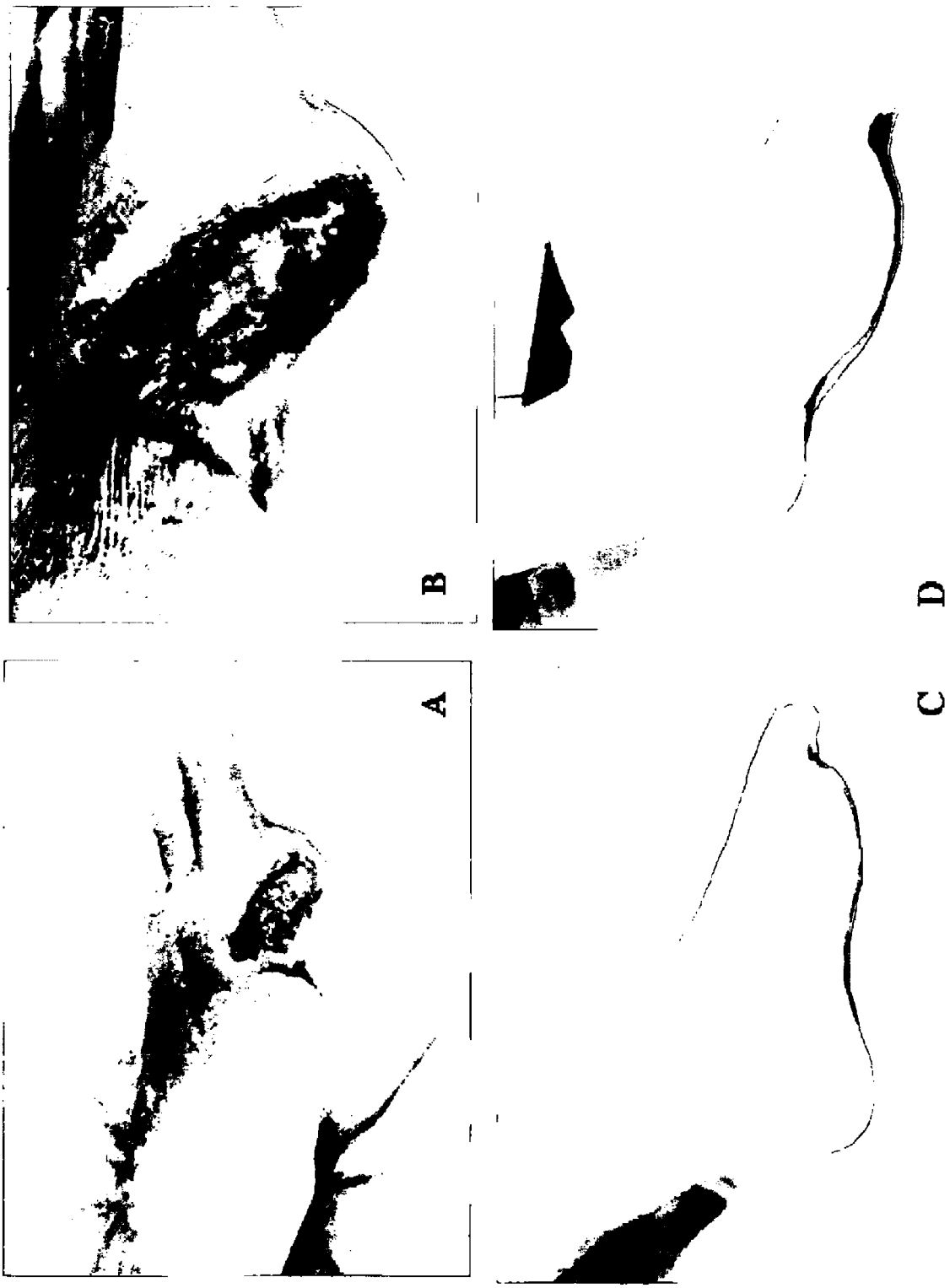
Figure 11: Patient 8 before (A and B) and 6 weeks after the treatment (C and D)

TREATMENT OF THROMBOANGIITIS OBLITERANS BY REMOVAL OF AUTOANTIBODIES

This is the U.S. national stage of International application PCT/EP2009/002993, filed Apr. 20, 2009 designating the United States and claims priority to European application EP08075309.8, filed Apr. 18, 2008, which is incorporated herein by reference in its entirety.

The invention relates to the use of a specific ligand for antibodies, preferably autoantibodies in the manufacture of a column for the treatment of thromboangiitis obliterans. The invention pertains furthermore to the apharesis column with at least one anti-IgG antibody for the treatment of thromboangiitis obliterans.

Polycellular organisms, especially mammals, and more particularly humans, cope with their environment via various biochemical and/or immunological regulatory mechanisms. For example, an important biochemical regulatory mechanism is the one that is responsible for maintaining constant a specific internal temperature in the organism. Another important regulatory mechanism provides cellular and humoral substances, such as antibodies, enabling the organism to cope successfully with microorganisms, parasites, but also, tumors or other diseases. Above all, the function of antibodies is based on the capability of distinguishing between "foreign" and "self". That is, the organism itself produces antibodies which are designed in such a way that endogenous structures such as tissues or organs are not attacked, but bind to bacteria, parasites or other exogenic components, thus initiating or supporting immunological reactions.

During biochemical development of an antibody response in the organism, somatic hypermutations of antibody-producing B cells occur during T cell-dependent immune response. Such mutations selectively involve immunoglobulin genes, being essential to the formation of precursor cells of antibody-forming cells with high affinity. It should be noted in this context that such mutation is a normal and essentially non-pathogenic process. However, mutations may also give rise to the formation of highly affine autoantibodies, thus doing damage to the organism.

Autoantibodies are closely associated with the development of autoimmune diseases or causally responsible for such diseases. Antibody-mediated autoimmune diseases also include diseases such as rheumatism or lupus erythematosus. Numerous autoimmune diseases, being highly inconvenient to affected persons, relate to important biochemical cycles in the organism.

The use of immunoapheresis treatment for cardiomyopathy and ITP is known in the state of art (WO 97/17980; Richter et al 1997 (XP-002492543)). Cardiomyopathy is a heart diseases which is not related to thromboangiitis obliterans, therefore there was not suggested at all to use the same or a similar treatment in both diseases.

Thromboangiitis obliterans (also known as Buerger's disease) is an acute inflammation and thrombosis (dotting) of arteries and veins of the hands and feet. It is strongly associated with use of tobacco products, primarily from smoking, but also from smokeless tobacco. There is a recurrent acute and chronic inflammation and thrombosis of arteries and veins of the hands and feet. The main symptom is pain in the affected areas. Ulcerations and gangrene in the extremities are common complications, often resulting in the need for amputation of the involved extremity.

The exact cause of Thromboangiitis obliterans/Buerger's disease is not known in the state of the art. It is seen most often in young to middle-aged men (ages 20-40) who are heavy smokers of cigarettes. Cases of this disease in non-smokers are very rare, hence, cigarette smoking is considered a causative factor. Approximately 40% of the patients have a history of inflammation of a vein (phlebitis), which may play a role in the development of Buerger's disease. The disease is mainly seen in the legs of affected persons, but may also appear in their arms. Early symptoms include decrease in the blood supply (arterial ischemia) and superficial (near the skin surface) phlebitis. The main symptom is pain in the affected areas. Onset of the disease is gradual and first occurs in the feet or hands. Inflammation occurs in small and medium-sized arteries and veins near the surface of the limb. In advanced cases, blood vessels in other parts of the body may be affected. There is a progressive decrease in the blood flow to the affected areas. The pulse in arteries of the feet is weak or undetectable. The lack of blood flow can lead to gangrene, which is decay of tissue due to restricted blood supply. A cold sensitivity in the hands, similar to that seen in Raynaud's disease, can develop. In this case, the hands turn color—white, blue, and then red—when exposed to the cold.

Disadvantageously, however, there is no known effective medication or surgery for thromboangiitis obliterans. Symptoms are treated, as there is no treatment for the disease. The only currently available treatment is amputation of the affected areas.

The object of the invention was therefore to provide means allowing easy, reliable and effective diagnosis and therapy of thromboangiitis obliterans.

The invention solves the above technical problem by using a device comprising a ligand, preferably a specific ligand, for antibodies, preferably IgG antibodies. It was however utterly surprising that ligands for autoantibodies may be applied in the therapy of thromboangiitis obliterans.

It was very surprising that thromboangiitis obliterans can be treated by the removal of IgG antibodies. It was not expected that the removal of IgG of all antibodies would have these superior results. It was not known in the state of art, that thromboangiitis obliterans can be treated as an autoimmune disease. Autoimmune diseases occur more often women, whereas thromboangiitis obliterans does affect mostly men. The association of thromboangiitis obliterans and tobacco consumption does also not suggest an autoimmune background. The finding that thromboangiitis obliterans can be treated with immune apheresis results from a lucky choice, since no the result was unforeseeable. Especially surprising was the fact that antibodies which recognize IgG antibodies directed against artery and/or vein tissue can be used to treat thromboangiitis obliterans. So far immune apheresis was not used to neutralize, eliminate or block antibodies against artery and/or vein tissue.

In a preferred embodiment, the invention therefore relates to the use of a specific ligand for human immunoglobulin in the manufacture of a column having said ligand coupled thereto for the treatment of a patient suffering from thromboangiitis obliterans, said treatment comprising passing plasma of the patient over the column under conditions which effect the binding of said specific ligand to immunoglobulin in the patient's plasma, thereby removing a significant portion of the immunoglobulin from the patient's plasma and reinfusing the plasma to the patient. In the context of the invention, the term "significant portion" is directed to an amount of autoantibodies whose removal from the plasma leads to an improvement of the patient's condition or to the non-appearance of a further aggravation. This improvement of the patient's condition relates to at least one of the aspects of thromboangiitis obliterans, known to a person skilled in the art.

It was very surprising, that columns known in the state of art can be used to solve the underlying problem. So far it was unknown that these columns can used to treat thromboangiitis obliterans.

In a further preferred embodiment of the invention, the specific ligand is an antibody-linked sepharose in a column which binds specific antibodies. These aspects of the invention are based on the conclusion made by the inventors, that thromboangiitis obliterans is caused by autoantibodies, especially by agonistic autoantibodies which lead to a potent vasoconstriction. It was surprising that linking the ligand to sepharose leads to superior results.

The invention also encompasses the use of a specific ligand in the manufacture of a column for extracorporal removal of autoantibodies directed against thromboangiitis obliterans structures—e.g. arteries or veins of the hands, arms, feet and legs—by removing immunoglobulins of any or all classes and subclasses, for the treatment of thromboangiitis obliterans. Such removal can be accomplished by using any specific ligands for human immunoglobulin coupled to an immunoaffinity chromatographic column. Such ligands include polyclonal and monoclonal anti-human immunoglobulin antibodies, fragments of such antibodies ($FAB_1$, $FAB_2$), recombinant antibodies or proteins, synthesized peptides, Protein A and Protein G.

Another aspect of the invention is therefore also the essentially unspecific removal of immunoglobulins from plasma taken from a patient suffering from thromboangiitis obliterans and reinfusing said plasma to the patient. The reinfused plasma may also contain those immunoglobulins which induce a positive effect in the context of the patient's immune system.

The invention also encompasses the use of more specific ligands in the manufacture of a column for extracorporal removal of specific IgG, IgM, IgA, IgE, IgD, IgY and/or IgW autoantibodies. This means that the removal of all antibodies or the removal of all or part of the autoantibodies or the removal of all or part of the specific IgG, IgM, IgA, IgE, IgD, IgY and/or IgW autoantibodies is part of the invention.

In another preferred embodiment the anti-IgG antibodies comprise a linker and/or a spacer selected from the group comprising α-aminocarboxylic acids as well as homo- and heterooligomers thereof, α, ω-aminocarboxylic acids and branched homo- or heterooligomers thereof, other aliphatic and/or aromatic amino acids, as well as linear and branched homo- or heterooligomers (peptides); amino-oligoalkoxyalkylamines; maleinimidocarboxylic acid derivatives; oligomers of alkylamines; 4-alkylphenyl derivatives; 4-oligoalkoxyphenyl or 4-oligoalkoxyphenoxy derivatives; 4-oligoalkylmercaptophenyl or 4-oligoalkylmercaptophenoxy derivatives; 4-oligoalkylaminophenyl or 4-oligoalkylaminophenoxy derivatives; (oligoalkylbenzyl)phenyl or 4-(oligoalkylbenzyl)phenoxy derivatives, as well as 4-(oligoalkoxybenzyl)phenyl or 4-(oligoalkoxybenzyl)phenoxy derivatives; trityl derivatives; benzyloxyaryl or benzyloxyalkyl derivatives; xanthen-3-yloxyalkyl derivatives; (4-alkylphenyl)- or ω-(4-alkylphenoxy)alkanoic acid derivatives; oligoalkylphenoxyalkyl or oligoalkoxyphenoxyalkyl derivatives; carbamate derivatives; amines; trialkylsilyl or dialkylalkoxysilyl derivatives; aliphatic or aromatic mono- or oligomercapto derivatives; alkyl or aryl derivatives and/or combinations thereof. Additionally, the SH group of the cysteine reacts with the double bound of the maleinimide group to form a covalent bound to a linker molecule. This linkage is could couple to another molecule or a solid phase.

In a preferred embodiment of the invention, antibodies directed against the IgG antibody are bound, complexed and/or neutralized by means of the above-mentioned inventive materials and products, apparatus, particularly the chromatography apparatus. For example, the column of the invention can be used in the detection of autoantibodies in serums of patients, using an ELISA or other immunological detection methods well-known to those skilled in the art. For detection, it can be advantageous, for example, when the autoantibodies are bound by biotinylated or otherwise coupled peptides and separated by streptavidin-coupled supports such as magnetic particles or plates. Such a method has been described in DE 102 56 897.9 which hereby is incorporated in the disclosure of the present application. More specifically, the separated autoantibodies are detected using IgG subtype-specific labelled antibodies.

The invention relates also to the use of a specific ligand for human immunoglobulins in the manufacture of a column coupled to said ligand for the treatment of a patient suffering from Thromboangiitis obliterans, said treatment comprising passing plasma of the patient, over the column under conditions which effect the binding of said specific ligand to immunoglobulin in the patient's plasma, thereby removing a significant portion of the immunoglobulin from the patient's plasma, and reinfusing the plasma to the patient.

In a preferred embodiment of the invention, treatment with the Ig-TheraSorb system effects the removal of a high proportion of antibodies of all classes and IgG-subclasses and therefore of antibodies directed against arteries and veins, preferably of the hands and feet. This treatment also removes antibodies of any other specificity against artery or vein tissue. It is postulated that removal of these autoantibodies is the basis for the efficacy of Ig-TheraSorb treatment of patients with Thromboangiitis obliterans. Also preferred is the use of Prosorba columns.

The treatment schedule foresees an initial series of Ig-TheraSorb immunoaphereses within a period of five consecutive days. The initial series of Ig-TheraSorb immunoaphereses can be followed by additional immunoaphereses if indicated as determined by autoantibody-monitoring and/or clinical symptoms. Surprisingly the method of the invention so effective that the patients do not need opiates or other pain killers anymore. The effect of the method last for more than one year, which is a great success compared to the treatment methods known in the state of art.

The invention encompasses extracorporeal removal of autoantibodies directed against artery or vein structures by removing immunoglobulins of any or all classes and subclasses, for the treatment of Thromboangiitis obliterans. Such removal can be accomplished by using any specific ligands for human immunoglobulin coupled to the Therasorb column.

The invention also encompasses more specific extracorporeal removal of autoantibodies against artery or vein structures, using constructs mimicking the antigen targets of the autoantibodies which are coupled to the Therasorb column. Such antigen-mimicking molecules include anti-idiotypic antibodies (polyclonal or monoclonal), fragments of such antibodies or sythesized peptides, like parts of receptor structures or other chemical substances.

Additionally, the invention relates also to the treatment of a patient suffering from Thromboangiitis obliterans, said treatment comprising the steps of
(a) providing a column coupled to a specific ligand for human immunoglobulin,
(b) passing plasma of the patient over the column under conditions which effect the binding of said specific ligand to immunoglobulin in the patient's plasma, thereby removing a significant portion of the immunoglobulin from the patient's plasma, and (c) reinfusing said plasma to the patient.

In a preferred embodiment, the treatment of a patient is characterized in that the specific ligand is selected from the group consisting of polyclonal anti-human immunoglobulin antibodies, monoclonal anti-human immunoglobulin antibodies, a fragment of such antibodies, recombinant molecules of the anti-body idiotype, synthesized peptides, Protein A and Protein G.

In another preferred embodiment of the treatment of a patient, the specific ligand recognizes antibodies directed against tissue of veins and arteries. Preferably, the specific ligand is an antigen-mimicking molecule selected from the group consisting of polyclonal and monoclonal antiidiotypic antibodies, fragments of such antibodies, and synthesized peptides.

It is preferred, that the specific ligand removes antibodies of any other specificity against artery or vein tissue. Surprisingly the removal of these autoantibodies is the basis for the efficacy of the treatment of patients with thromboangiitis obliterans.

Preferably, the specific ligand is a synthesized peptide mimicking a sequence of an antibody.

In the context of the invention is a treatment of a patient suffering from Thromboangiitis obliterans a preferred embodiment of the use of the specific ligand for human immunoglobulin in the manufacture of a column for the treatment of a patient.

The teachings of the present invention are characterised by the following features:
  departure from the beaten track
  a new perception of the problem
  satisfaction of a long-felt need or want
  hitherto all efforts of experts were in vain
  the simplicity of the solution, which proves inventive action, especially since it replaces a more complex doctrine
  the development of scientific technology followed another direction
  the achievement forwards the development
  misconceptions among experts about the solution of the according problem (prejudice)
  technical progress, such as: improvement, increased performance, price-reduction, saving of time, material, work steps, costs or resources that are difficult to obtain, improved reliability, remedy of defects, improved quality, no maintenance, increased efficiency, better yield, augmentation of technical possibilities, provision of another product, opening of a second way, opening of a new field, first solution for a task, spare product, alternatives, possibility of rationalisation, automation or miniaturisation or enrichment of the pharmaceutical fund
  special choice; since a certain possibility, the result of which was unforeseeable, was chosen among a great number of possibilities, it is a patentable lucky choice
  error in citations
  young field of technology
  combined invention; a combination of a number of known elements, with a surprising effect
  licensing
  praise of experts and
  commercial success Said advantages are shown especially in the preferential embodiments of the invention.

It is obviously known to a person skilled in the art that it is possible to provide functionally analogous means for the anti-IgG antibody of the invention. In the meaning of the invention, "functionally analogous means" are means which are functionally equivalent or equivalent to the peptides and nucleic acids of the invention. In order to check whether an analogous means is functionally equivalent (=equivalent) to the anti-IgG antibody of the invention, one must check whether the functionally analogous/equivalent means produces essentially the same function in essentially the same way with essentially the same outcome. That is, the outcome produced with the means of the invention may also be produced with the functionally analogous/equivalent means. A person skilled in the art can therefore easily and quickly verify whether a functionally analogous/equivalent means provided by them is covered by the invention. The functionally analogous means is covered by the invention if it may be used for solving the problem of the invention and if the solving of the problem of the invention can be carried out in essentially the same way as is claimed by the invention. While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the claims of the invention, including equivalents thereof. Therefore, as will be apparent to those skilled in the art to which the invention is addressed, the present invention may be embodied in forms other than those specifically disclosed without departing from the spirit or essential characteristics of the invention. The particular embodiments of the present invention as described are therefore to be considered in all respects as illustrative and not restrictive. The scope of the present invention is as set forth in the appended claims rather than being limited to the examples contained in the foregoing description.

Further to thromboangiitis obliterans, it is also possible to treat other diseases such as: undifferentiated connective tissue syndrome, antiphospholipid syndrome, different forms of vasculitis (polyarteritis nodosa, allergic granulomatosis and angiitis), Wegner's granulomatosis, Kawasaki disease, hypersensitivity vasculitis, Henoch-Schoenlein purpura, Behcet's Syndrome, Takayasu arteritis, Giant cell arteritis, polymyalgia rheumatica, essential (mixed) cryoglobulinemia, psoriasis vulgaris and psoriatic arthritis, diffuse fasciitis with or without eosinophilia, relapsing panniculitis, relapsing polychondritis, lymphomatoid granulomatosis, erythema nodosum, ankylosing spondylitis, myasthenia gravis, Reiter's syndrome, different forms of inflammatory dermatitis, skeletal muscle myopathy and primary pulmonary hypertension.

The method of the invention can be also used to treat, prevent or ameliorate one or more symptoms of disease in which blood vessels of the hands and feet become obstructed, vasculitis, reduced blood flow to the hand and foot tissues, inflammation and thrombosis of arteries and veins of the hands and feet myocardial diseases or pathological myocardial or vascular conditions such as amyloidosis or Gaucher's disease, Chagas cardiomyopathy, endocardial fibroelastosis, myocardial fibrosis, endomyocardial fibrosis, Kearns Syndrome, myocarditis, cardiovascular or vascular diseases, angiodysplasia, angiomatosis, Sturge-Weber Syndrome, angioneurotic edema, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, thrombosis, erythromelalgia, hemorrhoids, hepatic veno-occlusive disease, hypertension, hypotension, idiopathic pulmonary fibrosis, peripheral vascular diseases, phlebitis, pulmonary veno-occlusive disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, venous insufficiency and arterial occlusive diseases such as arteriosclerosis, intermittent claudication, carotid stenosis, fibromuscular dysplasias, mesenteric vascular occlusion, Moyamoya disease retinal artery occlusion, or atherosclerosis, any of which may be at an early stage or at a more advanced or late stage.

It was especially surprising, that the method of the invention can be also used to treat, prevent or ameliorate symptoms associated with high tobacco consumption.

Diseases and conditions which can also be treated by the method of the invention also include, but are not limited to, disease in which blood vessels of the hands and feet become obstructed, vasculitis, reduced blood flow to the hand and foot tissues, inflammation and thrombosis of arteries and veins of the hands and feet, Thromboangiitis obliterans-heart disease (e.g., arrhythmias, carcinoid heart disease, low cardiac output, cardiac tamponade, congestive heart failure, cardiac edema, left ventricular hypertrophy, right ventricular hypertrophy, myocardial diseases, myocardial ischemia, pneumopericardium, postpericardiotomy syndrome, rheumatic heart disease, hypertrophic cardiomyopathy, restrictive cardiomyopathy, myocardial ischemias (e.g., coronary artery disease, such as angina pectoris, coronary aneurysm, coronary arteriosclerosis, coronary thrombosis, coronary vasospasm and myocardial stunning), angiomatosis, Leriche's Syndrome, arterial occlusive diseases, arteritis, enarteritis, periarteritis nodosa, cerebrovascular disorders, diabetic angiopathies, diabetic retinopathy, embolisms, thrombosis, erythromelalgia, hepatic veno-occlusive disease, hypertension, hypotension, ischemia, peripheral vascular diseases, phlebitis, pulmonary veno-occlusive disease, retinal vein occlusion, telangiectasia, hereditary hemorrhagic telangiectasia, varicocele, varicose veins, varicose ulcer, vasculitis, venous insufficiency, Moyamoya disease, renal artery obstruction, retinal artery occlusion, cerebrovascular disorders (e.g., carotid artery diseases, cerebral amyloid angiopathy, cerebral aneurysm, cerebral anoxia, cerebral arteriosclerosis, cerebral artery diseases), thromboembolisms, thrombosis (e.g., coronary thrombosis, hepatic vein thrombosis, retinal vein occlusion, carotid artery thrombosis, sinus thrombosis, and thrombophlebitis), ischemic disorders (e.g., ischemic colitis, Morbus Crohn, colitis ulcerosa, compartment syndromes, anterior compartment syndrome, and peripheral limb ischemia), vasculitis (e.g., allergic cutaneous vasculitis, and Wegener's granulomatosis) and primary pulmonary hypertension.

The method of this present invention, selected and used as disclosed herein, is furthermore believed to be useful—for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, trauma or malignancy and whether associated with multi-organ failure or not), thrombotic thrombocytopenic purpura, thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and ischemia in general.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, hypersensitivity vasculitis, Schoenlein-Henoch purpura, allergic cutaneous vasculitis, and Wegener's granulomatosis.

It should be understood that various alternatives to the embodiments of the invention described herein may be employed in practicing the invention. It is intended that the claims of the invention define the scope of the invention and that the method and apparatus within the scope of these claims and their equivalents be covered thereby.

Without intending to be limiting, the invention will be explained in more detail with reference to the examples.

EXAMPLES

Example 1

Pilot Study

Thromboangiitis obliterans, for the purpose of this patent application, serves as a symptom picture with model nature for a large number of diseases that either until now have been taken under consideration for a long time, or that have not yet been considered as symptom pictures with autoimmunological background. Therapy strategies that lead to amelioration or even healing of this symptom picture should also prove beneficial for therapy of precisely these other diseases.

Within this context, a pilot study was conducted that included 10 patients with thromboangiitis obliterans (TAO) who had already undergone amputations within the course of their disease (e.g., amputation of toes, forefeet, lower legs, or fingers), or for whom indication had been established for such amputation owing to grievous pain, ischemia, or necrosis. At the point in time of immunoadsorption (IA), all patients were being administered opiates (morphine) in combination with maximum doses of non-steroidal antirheumatics (NSAR) for analgesic purposes. Mobility was severely limited for most patients—e.g., only a few meters of walking—and some were completely confined to a wheel chair.

The treatment schedule foresees an initial series of immunoapheresis treatments within a period of five consecutive days. The initial series of immunoapheresis treatments can be followed by additional immunoapheresis treatments if indicated as determined by autoantibody-monitoring and/or clinical symptoms.

Anti-human immunoglobulin coupled columns were used for the removal of immunoglobulin from the blood of human patients suffering from thromboangiitis obliterans.

Briefly, the tubing system of the primary separation system was first filled with sterile 0.9% NaCl. Two anti-human Ig columns (Ig-Therasorb, Baxter, Immunotherapy Division, Europe) were connected with the primary separation system. All tubing connections were made under aseptic conditions.

To remove the preservative solution from the columns, each column was rinsed before its first use with 5 liters sterile 0.9% NaCl solution, at a flow rate of 90 100 mL/min. For each subsequent use, it was sufficient to rinse each column with 2 liters of the sterile solution, at the same flow rate.

Before start of the procedure, the entire system was tested for absence of air bubbles and leaks, correct connections of the solutions, including the anticoagulants, correct installation of the programming of the device, functionality of the automatic clamps, and the safety system.

The appropriate canulae were connected to the left and right cubital veins of the patient. Blood samples were taken. The connection to the blood cell separator was put in place.

Anticoagulation was accomplished with either heparin or citrate (ACD-A or ACD-B). When citrate was the anti-coagulant, during the first half of the procedure, the citrate was used at a dilution of 1:22 to 1:18. In the second therapy phase, the dilution utilized was 1:12 to 1:8. Symptoms of hypocalcemia were monitored (paraesthesia in fingers or lips), and the administration of citrate was diminished accordingly. Calcium tablets could be given in cases of frank hypocalcemia.

After the venous puncture and the connection of the tubing system to the patient, the blood cell separator was filled with the patient's blood. The blood flow rate was kept between 50-90 mL/min. When a column with a volume of 100 ml was used, the liquid level was maintained at about 0.8 cm over the Sepharose in the column. After the stabilization of the separation process, the cell-free plasma was directed through the tubing system over the first column. It was important to keep the flow rate even and to monitor the plasma level over the Sepharose in the column. A higher plasma level was undesirable, because it would have led to a higher volume burden for the patient, and plasma loss due to plasma retention in the column.

Using a plasma flow rate of up to 40 mL/min, the column was loaded with as much plasma as possible during 15 minutes. Thereafter, the plasma flow was switched to the second column, which was likewise filled with as much plasma as possible in 15 minutes.

During the time of filling of the second column, the plasma in the first column was flushed out using sterile 0.9% NaCl at the plasma flow rate. One column volume of plasma was returned to the patient together with the blood cells which had been removed.

Also during filling of the second column, the first column was regenerated as follows: (1) A further rinse with 50 ml 0.9% NaCl at a flow rate of 100 mL/min; (2) Desorption of the bound immunoglobulin with one column volume of sterile 0.2 M glycine/HCl buffer, pH 2.8. The controller of the device prevented contact between this solution and the patient. The desorbed immunoglobulin was discarded. (3) Neutralization with one column volume of sterile PBS, pH 7.4. Testing of the neutralization using pH indicator paper. (4) Rinsing out of the PBS with at least one column volume of sterile 0.9% Nacl. The column was then ready for the next round of adsorption.

Then, the filling of the columns was again automatically switched. This procedure was repeated as many times as necessary to process the desired volume of plasma. The number of cycles used was chosen by the attending physician, according to the condition and needs of the patient. So far, within the inventors' clinical experience, it has been possible to process up to 3.5 times the extracorporeal volume of a given patient during one column procedure. Moreover, the number of cycles used was not limited by the binding capacity of the columns, but rather by the needs of the individual patient.

Results: Preliminary results showed that the IgG concentration in the subjects' blood was reduced by at least 70% to over 99% compared to starting concentrations. IgA and IgM levels were reduced by 70% to 90%.

There was no morbidity or mortality associated with the use of the column procedure. Plasma loss was typically low, and no plasma replacement was required.

In summary, immunoadsorption can be an alternative therapeutic principle for Thromboangiitis obliterans in the presence of circulating human antibodies. Immunoadsorption can remove a significant portion of a patient's plasma immunoglobulin. Herein, the term "significant portion" refers to at least 20% of the patient's immunoglobulin. In certain cases, it is desirable to remove up to 80%, and in certain cases more than 80%, preferably 90% of the patient's immunoglobulin.

Results:

(1) All patients became free of complaints during the course of the five-day treatment, with results measured on a pain scale of zero to ten (0=no pain; 10=maximum, intolerable pain). Already during the procedure itself—and in some cases even as soon as after the first 24 hours—complete relief from pain was achieved (FIG. 1). An initial value of approximately 8 was recorded under full analgesic therapy; the values thereafter, with no medication whatsoever.

(2) For all patients, it was possible to reduce or completely eliminate all analgesic medication, in the form of morphine or NSAR, in some cases already after the first 24 or 48 hours of therapy. One patient was an exception. After immunoadsorption therapy, he had no symptoms or pain whatsoever. As a result of remaining opiate addiction, however, he still required a low dose of morphine (FIGS. 3 and 4).

(3) The distance able to be walked by the patients—capability primarily involving the legs—was enhanced not only immediately after immunoadsorption, but also in the following months. Their walking distance dramatically increased: from only a few meters before IA, up to distances over 1,500 m (FIG. 2).

(4) The partial oxygen pressure ($tpO_2$) in the tissue of the involved extremities increased dramatically after immunoadsorption therapy, in most cases already after the second day of treatment. After completion of immunoadsorption, and during the following months, values for partial oxygen pressure reached normal levels (FIGS. 5 and 6).

(5) Partial carbon dioxide pressure ($tpCO_2$) in tissues demonstrated analogous behaviour and fell from pathologically high values to normal levels (FIGS. 7 and 8).

(6) For the two patients with forms of thromboangiitis obliterans primarily manifested in their arms, the result was a development comparable to the $tpO_2$ and $tpCO_2$ level changes summarised above (not shown in figures).

(7) The therapeutic effect of such treatment was of long-term nature and persisted (with one exception) for at least 6 months. During the follow-up examinations conducted until now, positive therapeutic effects have persisted for 12 months (FIGS. 1 to 10).

(8) FIGS. 9 and 10 summarise the results with respect to $tpO_2$ and $tpCO_2$ for all 10 patients on the most-afflicted extremity i.e., at the extremity that experienced the most severe pain, and/or demonstrated the most critical necrosis, and/or required amputation.

(9) For 3 of the 10 patients treated, necrosis completely healed within 8 weeks after immunoadsorption therapy although the necrotic lesions had already existed for several years, and although they had not healed under all therapeutic efforts (FIG. 11 a, b, c, d).

(10) Reynould syndrome, present in pronounced form among all patients, decisively improved among all 10 patients, as objectively disclosed with the aid of photoplethysmography. Even under cold provocation, pulsatile profiles became apparent at the terminal phalanges of the toes and fingers after immunoadsorption. Before immunoadsorption, there were no signs of pulsatile circulation.

(11) The patients subjectively experienced all the above-described alterations as warming of the respective extremities, as pain relief extending to complete absence of symptoms, as well as to further enhancement of subjectively experienced complaints that are not specific for the thromboangiitis obliterans syndrome: e.g., improvement in erectile dysfunction among 8 of the 10 male patients.

(12) The majority of the patients who had been unemployed or unable to work owing to their disease returned to their professions or to other paid jobs.

(13) It is essential to emphasise that the immunoadsorption therapy can be repeated at any time with the regenerable TheraSorb® columns. If kept at 4° C., they can be used again at any time for immunoadsorption therapy over a period of 5 years. This, however, has been unnecessary: neither for 10 patients after 6 months, nor for 4 patients after 12 months. Immunoadsorption therefore represents a cost-effective form of therapy, since the primary cost factor for this therapeutic procedure is purchase of the immunoadsorption columns.

LEGENDS TO FIGURES

FIG. 1 Pain scale
FIG. 2 distance walked
FIG. 3 NASR consumption
FIG. 4 Opiate consumption
FIG. 5 $tpO_2$ for right foot
FIG. 6 $tpO_2$ for left foot
FIG. 7 $tpCO_2$ for right foot
FIG. 8 $tpCO_2$ for left foot
FIG. 9: $tpO_2$ most afflicted extremity
FIG. 10 $tpCO_2$ most afflicted extremity
FIG. 11A-D Example of necrosis healing from Patient 8
11A and B: before IA
11C and D: 6 weeks after IA

The invention claimed is:

1. A method for treating a patient suffering from Thromboangiitis obliterans comprising:
   (a) providing a column having coupled thereto a specific ligand for human immunoglobulin,
   (b) passing plasma taken from a patient suffering from Thromboangiitis obliterans over the column under conditions which effect the binding of said specific ligand to immunoglobulin in the plasma of the patient,
   (c) removing a significant portion of immunoglobulin from the plasma, and
   (d) reinfusing the patient's plasma into the patient and thereby treating the patient,
   wherein said specific ligand is selected from the group consisting of polyclonal anti-human immunoglobulin antibodies, monoclonal anti-human immunoglobulin antibodies, a fragment of such antibodies, recombinant molecules of the antibody idiotype, synthesized peptides, Protein A and Protein G; and
   wherein said method:
      (i) reduces the amount of IgG, IgA, and IgM immunoglobulin in said patient's blood by at least 70 percent;
      (ii) at least 3 of: (A) reduces pain in said patient by at least 4 on a scale of 1-10; (B) increases walking distance by said patient by at least 40%; (C) improves pO2 in the extremities of said patient to normal levels; (D) reduces pCO2 in tissue of said patient to normal levels; and (E) reduces necrotic lesions in the extremities of said patient.

2. The method of claim 1 wherein said specific ligand recognizes autoantibodies directed against artery or vein tissue.

3. The method of claim 1 wherein said specific ligand recognizes autoantibodies directed against artery or vein tissue.

4. The method of claim 3 wherein said specific ligand is an antigen-mimicking molecule selected from the group consisting of polyclonal and monoclonal antiidiotypic antibodies, fragments of such antibodies, and synthesized peptides.

5. The method of claim 1, wherein the patient treated is a patient that displays symptoms of arterial ischemia and superficial phlebitis.

6. The method of claim 1, wherein the patient treated is a patient in which inflammation has occurred in small and medium-sized arteries of a limb of the patient.

7. The method of claim 6, wherein there is a progressive decrease in blood flow to said limb of said patient treated.

8. An immunoapheresis method comprising:
   treating a patient suffering from thromboangiitis obliterans by having the patient undergo a plurality of immunoapheresis procedures comprising
   passing the patient's plasma over a column having coupled thereto a specific ligand selected from the group consisting of a polyclonal or monoclonal anti-human immunoglobulin antibody or a fragment thereof, protein A and protein G, followed by reinfusion of the patient's plasma into the patient, and wherein the immunoapheresis procedure is conducted under conditions which promote the binding of the specific ligand to immunoglobulin in the plasma;
   wherein said method:
      (i) reduces the amount of IgG, IgA, and IgM immunglobulin in said patient's blood by at least 70 percent;
      (ii) at least 3 of: (A) reduces pain in said patient by at least 4 on a scale of 1-10; (B) increases walking distance by said patient by at least 40%; (C) improves pO2 in the extremities of said patient to normal levels; (D) reduces pCO2 in tissue of said patient to normal levels; and (E) reduces necrotic lesions in the extremities of said patient.

9. The method according to claim 8 wherein at least three immunoapheresis procedures are performed on the patient within a one or two week period.

10. The method according to claim 9 wherein the immunoapheresis procedure is conducted for at least once a day for five consecutive days.

11. The method according to claim 8 wherein the immunoapheresis procedure is conducted for at least once a day for five consecutive days.

12. The method of claim 8, wherein the patient treated is a patient that displays symptoms of arterial ischemia and superficial phlebitis.

13. The method of claim 8, wherein the patient treated is a patient in which inflammation has occurred in small and medium-sized arteries of a limb of the patient.

14. The method of claim 13, wherein there is a progressive decrease in blood flow to said limb of said patient treated.

* * * * *

UNITED STATES PATENT AND TRADEMARK OFFICE
CERTIFICATE OF CORRECTION

PATENT NO. : 8,663,147 B2
APPLICATION NO. : 12/988267
DATED : March 4, 2014
INVENTOR(S) : Gert Baumann It is certified that error appears in the above-identified patent and that said Letters Patent is hereby corrected as shown below:

In the Claims

Please replace lines 20 to 22, column 12 (ie, claim 2) with the following:

2. The method of claim 1, wherein said specific ligand is selected from the group consisting of polyclonal anti-human immunoglobulin antibodies, monoclonal anti-human immunoglobulin antibodies, a fragment of such antibodies, recombinant molecules of the antibody idiotype, synthesized peptides, Protein A and Protein G.

Signed and Sealed this
Twenty-fourth Day of February, 2015

Michelle K. Lee
*Deputy Director of the United States Patent and Trademark Office*